(12) United States Patent
Maldonado et al.

(10) Patent No.: US 10,888,635 B2
(45) Date of Patent: Jan. 12, 2021

(54) ABSORBENT ARTICLE HAVING ODOR ABSORBING MATERIAL

(71) Applicant: The Procter & Gamble Company, Cincinnati, OH (US)

(72) Inventors: Clarissa Maldonado, Cincinnati, OH (US); Kun Sun, Beijing (CN); Johannson Jimmy Tee, Jr., Mason, OH (US); Norman Scott Broyles, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 530 days.

(21) Appl. No.: 15/613,510

(22) Filed: Jun. 5, 2017

(65) Prior Publication Data

US 2017/0360983 A1    Dec. 21, 2017

(30) Foreign Application Priority Data

Jun. 16, 2016  (WO) ................ PCT/CN2016/085985
Apr. 7, 2017   (WO) ................ PCT/CN2017/079640

(51) Int. Cl.
*A61L 15/46*  (2006.01)
*A61F 13/84*  (2006.01)
(Continued)

(52) U.S. Cl.
CPC .......... *A61L 15/46* (2013.01); *A61F 13/5146* (2013.01); *A61F 13/51458* (2013.01);
(Continued)

(58) Field of Classification Search
CPC ............ A61F 13/51458; A61F 13/5146; A61F 13/535; A61F 13/539; A61F 13/8405;
(Continued)

(56) References Cited

U.S. PATENT DOCUMENTS 3,860,003 A    1/1975  Buell
4,472,328 A    9/1984  Sugimoto et al.
(Continued)

FOREIGN PATENT DOCUMENTS

CA    2185107 C    12/2000
GB    2531345      4/2016
(Continued)

OTHER PUBLICATIONS

Supplementary International Search Report, PCT/CN2017/079640, dated Mar. 18, 2019, 8 pages.
(Continued)

*Primary Examiner* — Michele M Kidwell
(74) *Attorney, Agent, or Firm* — Daniel S. Albrecht; Wednesday G. Shipp

(57) ABSTRACT

An absorbent article includes a chassis comprising a topsheet, a backsheet, and an absorbent core disposed between the topsheet and backsheet. The absorbent core contains superabsorbent polymer material and about 10% or less by weight of cellulosic fibers. The backsheet comprises a film comprising a plurality of micropores. The film comprises odor absorbing material disposed in one or more of the micropores.

19 Claims, 4 Drawing Sheets

(51) Int. Cl.
*A61F 13/535* (2006.01)
*A61L 15/18* (2006.01)
*A61F 13/514* (2006.01)
*A61F 13/51* (2006.01)
*A61F 13/539* (2006.01)
*B01J 20/18* (2006.01)

(52) U.S. Cl.
CPC .......... *A61F 13/535* (2013.01); *A61F 13/539* (2013.01); *A61F 13/8405* (2013.01); *A61L 15/18* (2013.01); *B01J 20/18* (2013.01); *A61F 2013/5109* (2013.01); *A61F 2013/51409* (2013.01); *A61F 2013/53908* (2013.01); *A61F 2013/8423* (2013.01); *A61L 2300/102* (2013.01)

(58) Field of Classification Search
CPC .... A61F 2013/5109; A61F 2013/51409; A61F 2013/53908; A61F 2013/8423; A61F 13/51401; A61F 13/51456; A61F 2013/8408; A61L 15/18; A61L 15/46; A61L 2300/102; B01J 20/18; A61S 13/51401
See application file for complete search history.

(56) References Cited

U.S. PATENT DOCUMENTS

| | | |
|---|---|---|
| 4,610,678 A | 9/1986 | Weisman et al. |
| 4,673,402 A | 6/1987 | Weisman et al. |
| 4,834,735 A | 5/1989 | Alemany et al. |
| 4,888,231 A | 12/1989 | Angstadt |
| 4,892,536 A | 1/1990 | DesMarais et al. |
| 4,990,147 A | 2/1991 | Freeland |
| 5,037,416 A | 8/1991 | Allen et al. |
| 5,137,537 A | 8/1992 | Herron et al. |
| 5,147,345 A | 9/1992 | Young et al. |
| 5,151,092 A | 9/1992 | Buell et al. |
| 5,200,247 A | 4/1993 | Wu et al. |
| 5,221,274 A | 6/1993 | Buell et al. |
| 5,260,345 A | 11/1993 | DesMarais et al. |
| 5,269,775 A | 12/1993 | Freeland et al. |
| 5,342,338 A | 8/1994 | Roe et al. |
| 5,387,207 A | 2/1995 | Dyer et al. |
| 5,397,316 A | 3/1995 | LaVon et al. |
| 5,407,979 A | 4/1995 | Wu-Pai et al. |
| 5,554,145 A | 9/1996 | Roe et al. |
| 5,569,234 A | 10/1996 | Buell et al. |
| 5,571,096 A | 11/1996 | Dobrin et al. |
| 5,575,783 A | 11/1996 | Clear et al. |
| 5,580,411 A | 12/1996 | Nease et al. |
| 5,607,414 A | 3/1997 | Richards et al. |
| 5,607,760 A | 3/1997 | Roe |
| 5,609,587 A | 3/1997 | Roe |
| 5,635,191 A | 6/1997 | Roe et al. |
| 5,643,588 A | 7/1997 | Roe et al. |
| 5,700,254 A | 12/1997 | McDowall et al. |
| 5,769,832 A * | 6/1998 | Hasse ............... A61F 13/581 604/359 |
| 5,865,823 A | 2/1999 | Curro |
| 6,004,306 A | 12/1999 | Roe et al. |
| 6,107,537 A | 8/2000 | Elder et al. |
| 6,120,487 A | 9/2000 | Ashton |
| 6,177,607 B1 | 1/2001 | Blaney et al. |
| 6,365,794 B1 * | 4/2002 | Dabi ............... A61F 13/023 604/354 |
| 6,410,129 B2 | 6/2002 | Zhang et al. |
| 6,492,574 B1 * | 12/2002 | Chen ............... A61F 13/47218 604/378 |
| 6,534,149 B1 | 3/2003 | Daley et al. |
| 6,613,955 B1 * | 9/2003 | Lindsay ............ A61F 13/4704 604/378 |
| 6,632,212 B1 | 10/2003 | Morman et al. |
| 6,677,258 B2 | 1/2004 | Carroll et al. |
| 7,163,529 B2 * | 1/2007 | Mocadlo ............ A61F 13/4755 604/359 |
| 7,446,132 B2 | 11/2008 | Carcich |
| 7,806,883 B2 | 10/2010 | Fossum et al. |
| 7,819,853 B2 | 10/2010 | Desai et al. |
| 8,618,350 B2 | 12/2013 | Mansfield et al. |
| 8,735,646 B2 | 5/2014 | Beruda et al. |
| 8,795,809 B2 | 8/2014 | Mansfield |
| 8,822,752 B2 | 9/2014 | Fukae et al. |
| 9,000,254 B2 | 4/2015 | Rinnert et al. |
| 2002/0018761 A1 * | 2/2002 | Moscherosch ......... A61L 15/18 424/76.1 |
| 2003/0022573 A1 * | 1/2003 | Cintio ............... A61L 28/0019 442/96 |
| 2006/0246272 A1 * | 11/2006 | Zhang ................. B32B 5/18 428/304.4 |
| 2007/0049891 A1 * | 3/2007 | Clark, Jr. ........... A61F 13/5513 604/385.13 |
| 2007/0213412 A1 * | 9/2007 | Bacon ................. A61F 13/51 516/53 |
| 2009/0258210 A1 | 10/2009 | Autran et al. |
| 2010/0080834 A1 * | 4/2010 | Lori ................... A61F 13/8405 424/409 |
| 2010/0310810 A1 * | 12/2010 | Bond .................. B32B 27/32 428/74 |
| 2012/0237746 A1 | 9/2012 | O'Donnell et al. |
| 2012/0316526 A1 | 12/2012 | Rosati et al. |
| 2013/0158491 A1 * | 6/2013 | Caputi ............... A61F 13/5611 604/359 |
| 2015/0065973 A1 | 3/2015 | Roe et al. |
| 2015/0065975 A1 | 3/2015 | Roe et al. |
| 2015/0065976 A1 | 3/2015 | Roe et al. |
| 2015/0104627 A1 | 4/2015 | O'Donnell et al. |

FOREIGN PATENT DOCUMENTS

| | | |
|---|---|---|
| JP | 2008302138 A | 12/2008 |
| WO | WO 95/16746 | 6/1995 |
| WO | WO 97/46192 | 12/1997 |
| WO | WO 02/067809 | 4/2003 |
| WO | WO 2007/067110 | 6/2007 |

OTHER PUBLICATIONS

Bazemore, R. P., Nov. 15, 2011, "Odors and Packaging Materials", www.volatileanalysis.com.
International Search Report, PCT/CN2016/085985, dated Mar. 22, 2017, 14 pages.
EP Search Report, dated Feb. 4, 2020, 7 pages.

* cited by examiner

ABSORBENT ARTICLE HAVING ODOR ABSORBING MATERIAL

FIELD OF THE INVENTION

The present invention relates to articles comprising an odor absorbing material, and in particular articles having a film which comprises an odor absorbing material.

BACKGROUND OF THE INVENTION

Absorbent articles for receiving and retaining bodily discharges such as urine or feces are well known in the art. Examples of these include disposable diapers, training pants and adult incontinence articles. Typically, disposable diapers comprise a liquid pervious topsheet that faces the wearer's body, a liquid impervious backsheet that faces the wearer's clothing and an absorbent core interposed between the liquid pervious topsheet and the backsheet.

Some materials in absorbent articles contain petrochemicals. Such materials include adhesives, inks, elastics (e.g., elastics containing styrene) and binding agents. Over time, these materials can release volatile organic compounds, which may result in unpleasant odors such as smells associated with paint, solvent, glue or chemicals. Absorbent articles with such odors may be mistakenly perceived as poor quality or unsafe.

As improvements are made to absorbent articles, the likelihood of unwanted odors may increase. For instance, the inclusion of additional elastic materials in the waist area or leg cuffs to better secure the article to the wearer may increase the potential for unwanted odors stemming from those areas. Likewise, the reduction of pulp material in absorbent cores may result in additional adhesive or immobilizing agents to secure superabsorbent material, which in turn may increase the potential for odors over time.

While perfumes have been used to mask such odors, consumers often desire perfume-less products. Moreover, manufacturers require a means of resolving the odor issue without excessive costs, equipment changes or inefficiencies. Therefore, there is a need for an absorbent article having desired improvements (such as fit enhancements, thinner structures, etc.) but reduced odor. Likewise, there is a need to provide an efficient and cost-effective means of providing improved odor control.

SUMMARY OF THE INVENTION

In an embodiment, an absorbent article includes a chassis having a topsheet, a backsheet, and an absorbent core disposed between the topsheet and backsheet. The absorbent core includes absorbent particulate polymer material and about 10% or less by weight of cellulosic fibers. The backsheet may include a film comprising a plurality of micropores and odor absorbing material disposed in one or more of the micropores.

In a further embodiment, an absorbent article includes a chassis comprising a topsheet, a backsheet, and an absorbent core disposed between the topsheet and backsheet. The article further includes one or more adhesives forming an aggregate adhesive content and an odor absorbing material disposed in the backsheet, wherein the odor absorbing material forms an aggregate odor absorber content. The ratio of the aggregate odor absorbent content to the aggregate adhesive content is at from about 0.5% to about 10%.

In another embodiment, an absorbent article includes a first waist region, a second waist region, a crotch region disposed between the first and second waist regions. The article further includes a chassis comprising a topsheet, a backsheet, and an absorbent core disposed between the topsheet and backsheet. A first elasticized waist feature is joined to the chassis and disposed in the first waist region, and a second elasticized waist feature is joined to the chassis disposed in the second waist region. The backsheet comprises an odor absorbing material comprising zeolite.

DETAILED DESCRIPTION OF THE INVENTION

Definitions

Figure 1:
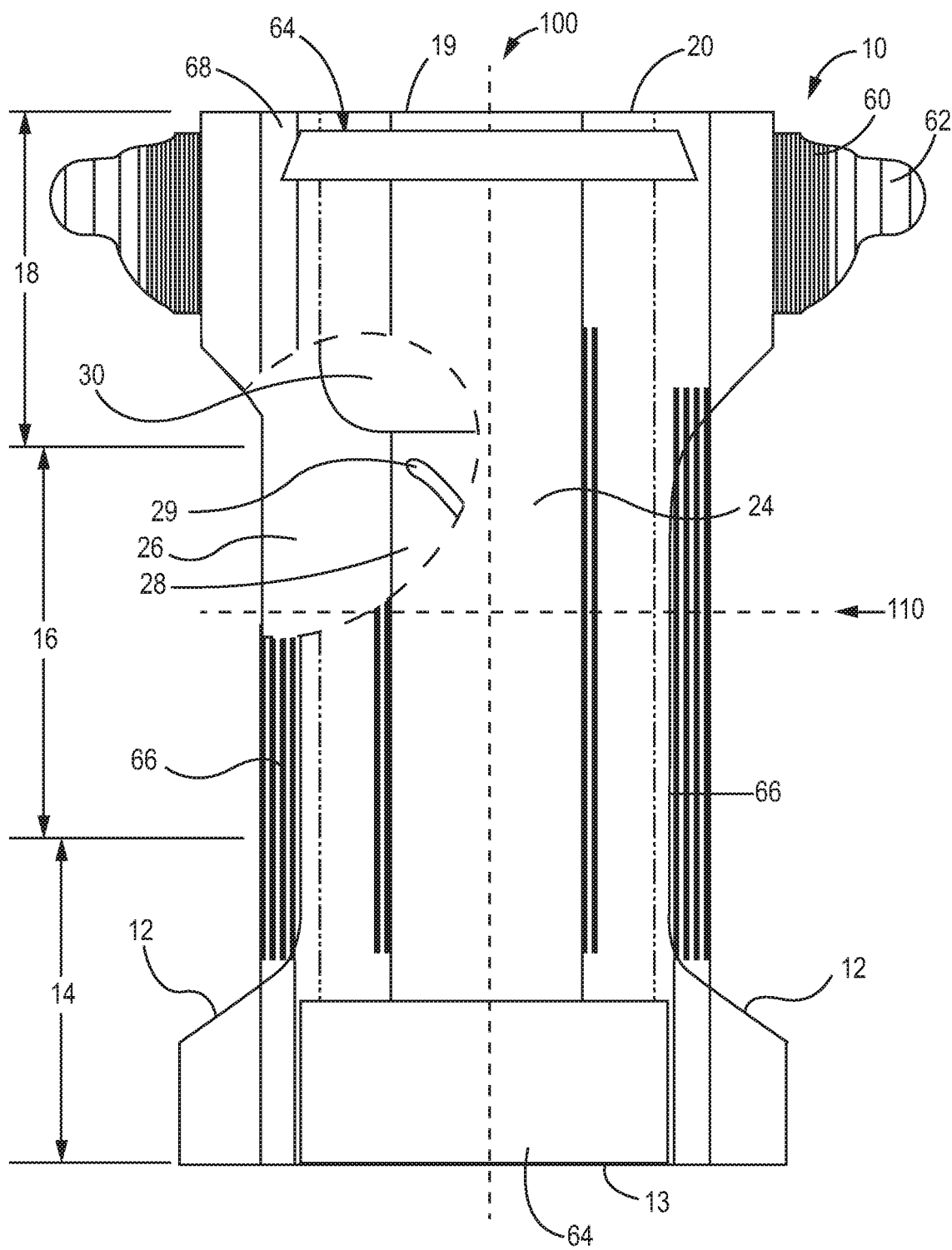
FIG. 1 is a schematic plan view of an exemplary embodiment of an absorbent article as detailed herein. The absorbent article is shown in a flat, uncontracted state.

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Activation" is the mechanical deformation of a plastically extensible material that results in permanent elongation of the extensible material, or a portion of the extensible material, in the direction of activation in the X-Y plane of the material. For example, activation occurs when a web or portion of a web is subjected to a stress that causes the material to strain beyond the onset of plasticity, which may or may not include complete mechanical failure of the material or portion of the material. Activation of a laminate that includes an elastic material joined to a plastically extensible material typically results in permanent deformation of the plastic material, while the elastic material returns substantially to its original dimension.

"Diaper" refers to an absorbent article generally worn by infants and incontinent persons about the lower torso so as to encircle the waist and legs of the wearer and that is specifically adapted to receive and contain urinary and fecal waste. As used herein, term "diaper" also includes "pants" which is defined below.

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Disposed" refers to an element being located in a particular place or position.

"Elongatable," "extensible," or "stretchable" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

"Film" means a sheet-like material wherein the length and width of the material far exceed the thickness of the material (e.g., 10×, 50×, or even 1000× or more). Films are typically liquid impermeable but may be configured to be breathable.

"Joined" refers to configurations whereby an element is directly secured to another element by affixing the element directly to the other element and to configurations whereby an element is indirectly secured to another element by affixing the element to intermediate member(s) which in turn are affixed to the other element.

A "nonwoven" is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. Nonwovens may include hydroentangled nonwovens. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding. The basis weight of nonwoven fabrics is usually expressed in grams per square meter (gsm).

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

"Substantially cellulose free" is used herein to describe an article, such as an absorbent core, that contains less than 10% by weight cellulosic fibers, less than 5% cellulosic fibers, less than 1% cellulosic fibers, no cellulosic fibers, or no more than an immaterial amount of cellulosic fibers. An immaterial amount of cellulosic material would not materially affect the thinness, flexibility, or absorbency of an absorbent core.

"Substantially continuously distributed", as used herein, refers to absorbent particulate polymer material that is arranged across the absorbent particulate polymer material area. Optionally, the absorbent particulate polymer material may be arranged such that the substrate layers do not touch in various zones. In one embodiment, the substrate layers may touch in the peripheral areas outside the absorbent particulate polymer material area. It is important to note that the thermoplastic material used in the present invention does not interrupt the substantially continuously distributed absorbent particulate polymer material. Thus, the substantially continuously distributed absorbent particulate polymer material includes the thermoplastic material.

"X-Y plane" means the plane defined by the MD and CD of a moving web or the length and width of a piece of material. The Z-direction is perpendicular to the X-Y plane.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor (i.e., may be "vapor-permeable").

"Wt %" refers to the percentage weight of a specific component relative to the entire composition.

Absorbent Article

FIG. 1 is a plan view of an absorbent article 10 according to a certain embodiment of the present invention. The article 10 is shown in its flat out, uncontracted state (i.e., without elastic induced contraction) and portions of the article 10 are cut away to more clearly show the underlying structure of the article 10. A portion of the article 10 that contacts a wearer is facing the viewer in FIG. 1. The absorbent article 10 includes a longitudinal centerline 100 and a lateral centerline 110.

The absorbent article 10 has a first waist region 14, a second waist region 18 opposed to the first waist region 14, and a crotch region 16 located between the first waist region 14 and the second waist region 18. The waist regions 14 and 18 generally comprise those portions of the absorbent article 10 which, when worn, encircle the waist of the wearer. The waist regions 14 and 18 may include elastic materials such that they gather about the waist of the wearer to provide improved fit and containment. The crotch region 16 is the portion of the absorbent article 10 which, when the absorbent article 10 is worn, is generally positioned between the legs of the wearer.

The article 10 comprises a chassis 20. The chassis may have opposing longitudinal edges 12 that are oriented generally parallel to the longitudinal centerline 100. However, for better fit, longitudinal edges 12 may be curved or angled to produce, for example, an "hourglass" shape article when viewed in a plan view as shown in FIG. 1. The chassis 20 may have opposing lateral edges 13, 19 (i.e., the first waist edge 13 and second waist edge 19) that are oriented generally parallel to the lateral centerline 110.

The chassis 20 may comprise a liquid permeable topsheet 24, a backsheet 26, and an absorbent core 28 between the topsheet 24 and the backsheet 26. The topsheet 24 may be joined to the core 28 and/or the backsheet 26. The backsheet 26 may be joined to the core 28 and/or the topsheet 24. It should be recognized that other structures, elements, or substrates may be positioned between the core 28 and the topsheet 24 and/or backsheet 26. In some embodiments, an acquisition-distribution system 30 is disposed between the topsheet 26 and the absorbent core 28.

In certain embodiments, the chassis 20 comprises the main structure of the absorbent article 10 with other features added to form the composite absorbent article structure. While the topsheet 24, the backsheet 26, and the absorbent core 28 may be assembled in a variety of well-known configurations, absorbent article configurations are described generally in U.S. Pat. Nos. 3,860,003; 5,151,092; 5,221,274; 5,554,145; 5,569,234; 5,580,411; and 6,004,306.

Topsheet

The topsheet 24 is generally a portion of the absorbent article 10 that may be positioned at least in partial contact or close proximity to a wearer. Suitable topsheets 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 24 is generally supple, soft feeling, and non-irritating to a wearer's skin. Generally, at least a portion of the topsheet 24 is liquid pervious, permitting liquid to readily penetrate through the thickness of the topsheet 24. One topsheet 24 useful herein is available from BBA Fiberweb, Brentwood, Tenn. as supplier code 055SLPV09U. The topsheet 24 may be apertured.

Any portion of the topsheet 24 may be coated with a lotion or skin care composition as is known in the art. Non-limiting examples of suitable lotions include those described in U.S. Pat. Nos. 5,607,760; 5,609,587; 5,635, 191; and 5,643,588. The specific examples are not limiting, as any lotion or skin care composition known in the art may be utilized. The topsheet 24 may be fully or partially elasticized or may be foreshortened so as to provide a void space between the topsheet 24 and the core 28. Exemplary structures including elasticized or foreshortened topsheets are described in more detail in U.S. Pat. Nos. 4,892,536; 4,990,147; 5,037,416; and 5,269,775.

Acquisition Distribution System

The absorbent article may comprise an ADS 30. One function of the ADS is to quickly acquire one or more of the fluids and distribute them to the absorbent core in an efficient manner. The ADS may comprise one, two or more layers, which may form a unitary layer or may remain as discrete layers which may be attached to each other. In an example, the ADS may comprise a distribution layer and/or an acquisition layer disposed between the absorbent core and the topsheet. Suitable ADS are described in WO 2000/59430, WO 95/10996, U.S. Pat. No. 5,700,254, and WO 02/067809, for example. One or more layers in the ADS may comprise material free zones as disclosed in U.S. patent application Ser. Nos. 14/467,092, 14/467,095 and 14/467,102. In such zones, the topsheet or another layer of the article may be joined to the absorbent core. The components may be joined by an adhesive bond.

Absorbent Core

The absorbent core is typically the component of the article having the most absorbent capacity. An exemplary absorbent core 28 of the invention is shown in isolation in FIG. 2A. The absorbent core 28 comprises absorbent material 36, which is typically enclosed within a core wrap 34. Typical core wraps comprise two substrates 34, 34' which are attached to another, but the core wrap may also be made of a single substrate folded around the absorbent material, or may comprises several substrates. When two substrates are used, these may be typically attached to another along at least part of the periphery of the absorbent core to form a seal. The substrates are advantageously attached to another to form a seal along all the edges of the core. Typical seals are the so-called C-wrap (i.e., flaps extending over the opposed edges of the core which are then folded over the other substrate, illustrated in FIG. 2A) and sandwich wrap (i.e., the first and second substrates both have material extension outwardly of the absorbent material deposition area which are then sealed flat along the whole or parts of the periphery of the core).

The front side 280 and back side 282 of the core wrap (see FIG. 3) may then also be sealed for example by gluing the first substrate and second substrate to another to provide complete enclosing of the absorbent material across the whole of the periphery of the core. The terms "seal" and "enclosing" are to be understood in a broad sense. The seal does not need to be continuous along the whole periphery of the core wrap but may be discontinuous along part or the whole of it, such as formed by a series of seal points spaced on a line. Typically, a seal may be formed by gluing and/or thermal bonding. The core wrap may also be formed by a single substrate which may enclose the absorbent material as in a parcel wrap and be for example sealed along the front side and back side of the core and one longitudinally extending seal.

The core wrap may be formed by any materials suitable for enclosing the absorbent material. Typical substrate materials used in the production of conventional cores may be used, in particular nonwovens but also paper, tissues, films, wovens, or laminate of any of these.

The absorbent material 36 may comprise an absorbent particular polymer material 38. The absorbent material may comprise relatively high amount of absorbent particular polymer material 38 enclosed within the core wrap. By "absorbent material" it is meant a material which has some absorbency property or liquid retaining properties, such as superabsorbent polymer material and cellulosic fibers. Typically, adhesives used in making absorbent cores have no absorbency properties and are not considered as absorbent material. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

In certain embodiments, the absorbent core 28 may be substantially cellulose free. In one embodiment, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core.

Figure 2A:
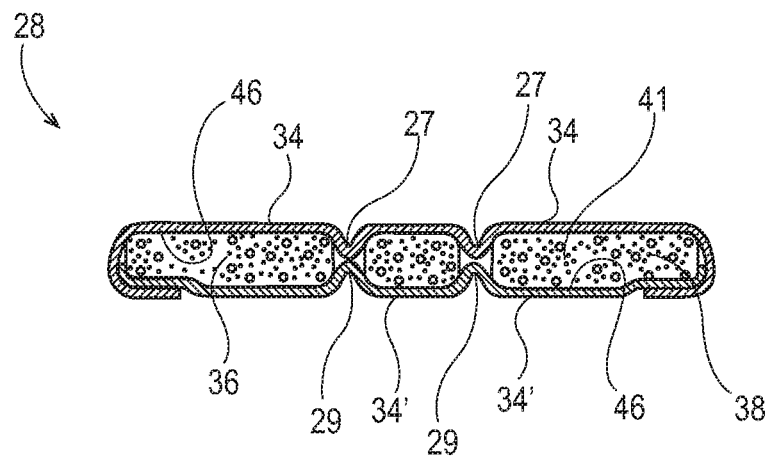
FIG. 2*a* is a schematic cross sectional view of an absorbent core in accordance with an embodiment of this invention.
Figure 2B:
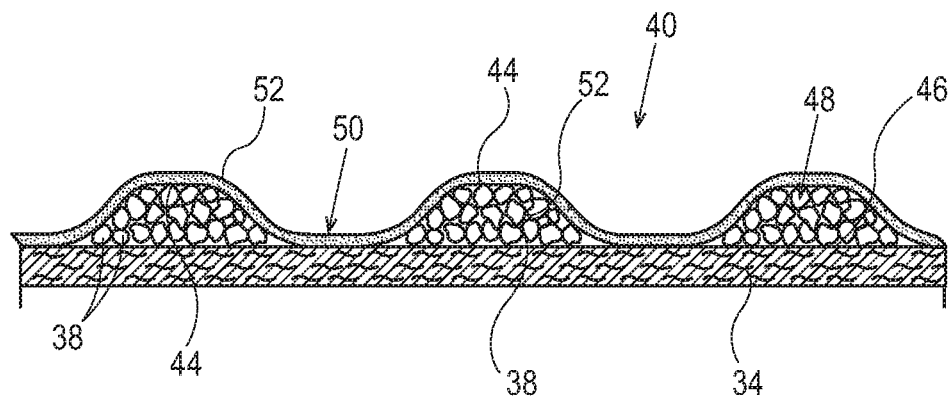
FIG. 2*b* is a partial schematic cross sectional view of an exemplary embodiment of an absorbent core layer.
Figure 2C:
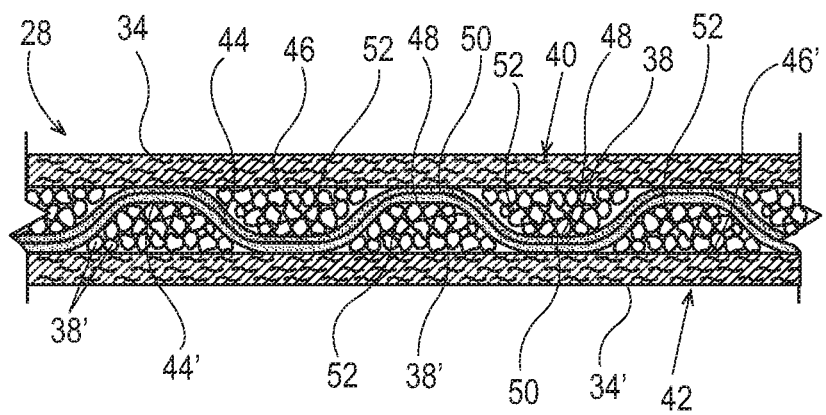
FIG. 2*c* is a partial schematic cross sectional view of an exemplary embodiment of absorbent core comprising a combination of absorbent core layers.

Further to the above, the absorbent core 28 may comprise one or more absorbent layers 40, 42 as depicted in FIGS. 2A-2C. An absorbent layer 40 may include a substrate 34, absorbent particulate polymer material 38 deposited on the substrate 34, and thermoplastic material 44 covering the absorbent particulate polymer material and immobilizing the absorbent particulate polymer material 38 on the substrate 34. The absorbent particulate polymer material 38 may be substantially continuously distributed across the absorbent particulate polymer material area 41. A second substrate 34' may be used with the substrate 34 to enclose the absorbent material. An auxiliary glue 46 may be applied between a substrate 34, 34' and the absorbent material.

Alternatively, the core 28 may comprise multiple layers. As shown in FIG. 2C, a first absorbent layer 40 comprises a substrate 34, an absorbent particular polymer material 38 on the substrate 34, and a thermoplastic composition 44 on the absorbent particulate polymer material 40 and at least portions of the first substrate 34, immobilizing the absorbent particulate polymer material 38 on the first substrate 34. According to another embodiment, the first absorbent layer 40 of the absorbent core 28 may also include a cover layer on the thermoplastic composition 44. The thermoplastic composition may comprise a thermoplastic adhesive composition. Likewise, the second absorbent layer 42 of the absorbent core 28 may also include a substrate 34', an absorbent particulate polymer material 38' on the second substrate 34', and a thermoplastic composition 44' on the absorbent particulate polymer material 38' and at least a portion of the second substrate 34' for immobilizing the absorbent particulate polymer material 38' on the second substrate 34'. The second absorbent layer 42 may also include a cover layer on the thermoplastic composition 44'. Further, an auxiliary glue 46 may be applied between one or both substrates and the absorbent material.

As illustrated in FIGS. 2B and 2C, the absorbent particulate polymer material 38 and 38' is deposited on the respective substrates 34 and 34' in clusters 52 of particles to form a grid pattern comprising land areas 48 and junction areas 50 between the land areas 48. The junction areas 48 in the grid pattern contain little or no absorbent particulate polymer material. The land areas 48 and junction areas 50 can have a variety of shapes including, but not limited to, circular, oval, square, rectangular, triangular, and the like.

The first and second absorbent layers 40 and 42 may be combined together to form the absorbent core 28 such that the grid patterns of the respective first and second absorbent layers are offset from one another along the length and/or width of the absorbent core 28. The respective grid patterns may be offset such that the absorbent particulate polymer material is substantially continuously distributed across the absorbent particulate polymer area 41. In a certain embodiment, absorbent particulate polymer material 38, 38' is substantially continuously distributed across the absorbent particulate polymer material area 41 despite the individual grid patterns comprising absorbent particulate polymer material 38, 38' discontinuously distributed across the first and second substrates 40, 42 in clusters 46. In a certain embodiment, the grid patterns may be offset such that the land areas 48 of the first absorbent layer 40 face the junction areas 50 of the second absorbent layer 42 and vice versa such that the resulting combination forms a substantially continuous layer of absorbent particular polymer material. In a certain embodiment, respective grid patterns of the first and second absorbent layer 40 and 42 may be substantially the same.

The thermoplastic material 44 may serve to cover and at least partially immobilize the absorbent particulate polymer material 38. In one embodiment of the present invention, the thermoplastic material 44 can be disposed essentially uniformly within the absorbent particulate polymer material 38. However, in a certain embodiment, the thermoplastic material 44 may be provided as a fibrous layer which is at least partially in contact with the absorbent particulate polymer material 38 and partially in contact with the substrate layer(s) 34, 34'. As shown in FIGS. 2A-2C, a layer of fibrous thermoplastic material 44 is laid down onto the layer of absorbent particulate polymer material 38, such that the thermoplastic material 44 is in direct contact with the absorbent particulate polymer material 38, but also in direct contact with the substrate 34 where the substrate is not covered by the absorbent particulate polymer material 38. This imparts an essentially three-dimensional structure to the fibrous layer of thermoplastic material 44, which in itself is essentially a two-dimensional structure of relatively small thickness, as compared to the extension in length and width directions. In other words, the thermoplastic material 44 undulates between the absorbent particulate polymer material 38 and the surfaces of the substrate 34.

According to certain embodiments, the thermoplastic material 38 can comprise any thermoplastic material, including, but not limited to adhesive thermoplastic materials, also referred to as hot melt adhesives. Some initially thermoplastic materials may later lose their thermoplasticity due to a curing step, e.g., initiated via heat, UV radiation, electron beam exposure or moisture or other means of curing, leading to the irreversible formation of a crosslinked network of covalent bonds. Those materials having lost their initial thermoplastic behavior are herein also understood as thermoplastic materials. Where the core 28 comprises multiple layers, said layers may comprise the same thermoplastic material or different thermoplastic materials.

The attachment of the top side and bottom side of the core wrap may be provided by one or more adhesive material, in particular one or more layers of auxiliary glue 46 and/or one or more layers of thermoplastic adhesive material 44. These glues may therefore serve the dual function of immobilizing the absorbent material and attach the top side and the bottom side of the core together. An auxiliary glue 46 may be applied between one or both substrates and the absorbent layers, as well as adhesive thermoplastic material 44 on each absorbent layer.

Figure 3:
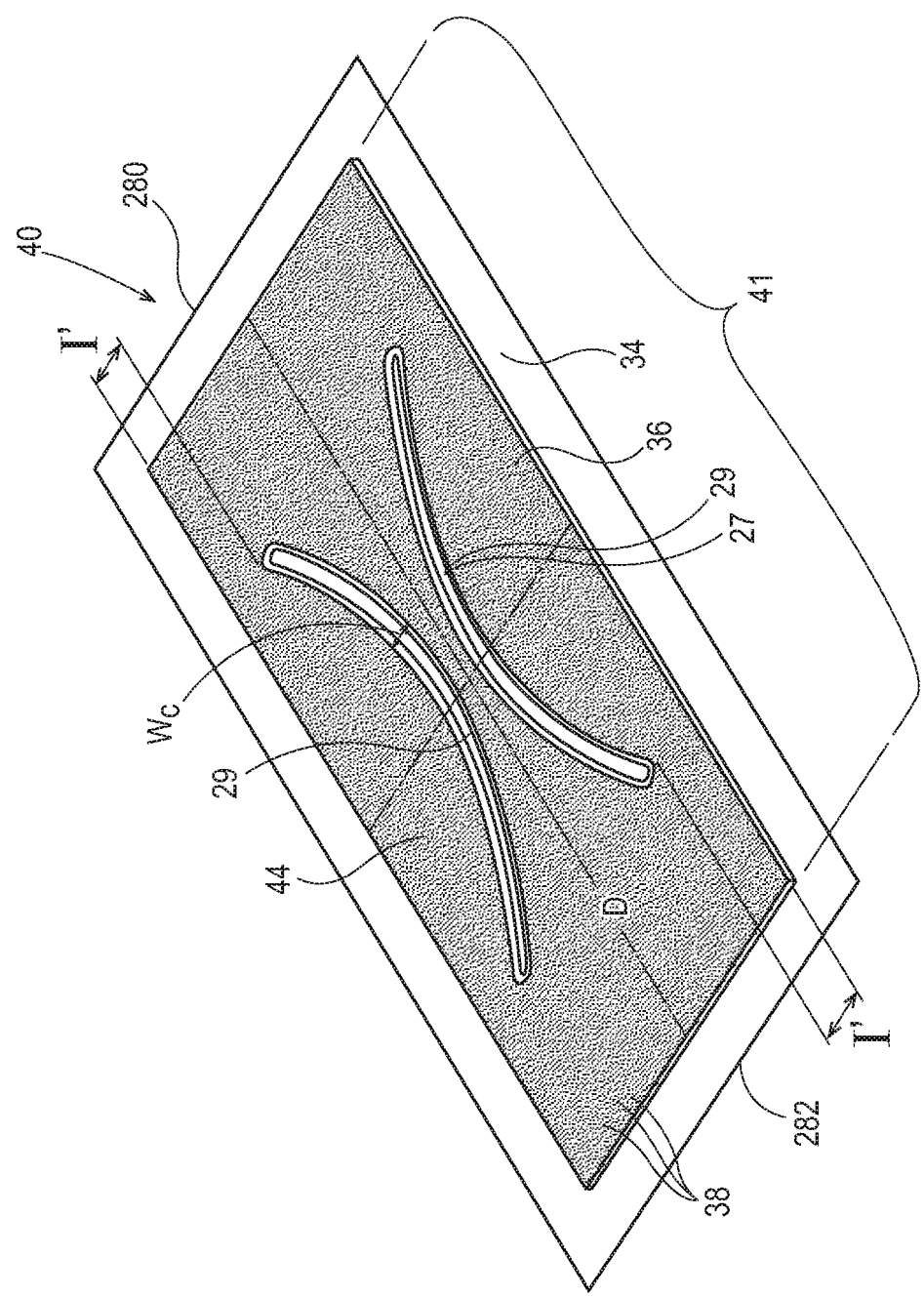
FIG. 3 is a schematic plan view of an exemplary embodiment of an absorbent core.

In some embodiments, the absorbent core may comprise one or more channels 29, wherein said channels are substantially free of absorbent particulate polymer material 38 as shown for example in FIGS. 2A and 3. The channels 29 may extend longitudinally or laterally. The absorbent core may further comprise two or more channels. In one non-limiting example, two channels are symmetrically disposed about the longitudinal axis. The top side of the core wrap (i.e., substrate 34) may be attached to the bottom side of the core wrap 34' through a channel, along a bond 27. When the absorbent material absorbs a liquid, it swells in proportion and the core wrap gradually forms a three-dimensional channel along the bonded area.

The channels, in particular when present as one or more symmetrical pair(s) relative to the longitudinal axis, may be spaced apart from one another over their whole longitudinal dimension. The smallest spacing distance, D, may be for example at least 5 mm, or at least 10 mm, or at least 16 mm.

Furthermore, in order to reduce the risk of fluid leakages, the channels 29 may advantageously not extend up to any of the edges of the absorbent material deposition area 41, and are therefore surrounded by and fully encompassed within the absorbent material deposition area 41. Typically, the smallest distance, I', between a channel 29 and the closest edge of the absorbent material deposition area is at least 5 mm.

Each channel may have a width Wc along at least part of its length which is at least 2 mm, or at least 3 mm or at least 4 mm, up to for example 20 mm, or 16 mm or 12 mm. The width Wc of each channel may be constant through substantially its whole length or may vary along its length.

Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; 5,397,316, and U.S. patent application Ser. No. 13/491,642 and 62/210,100.

Backsheet

The backsheet 26 is generally positioned such that it may be at least a portion of the garment-facing surface of the absorbent article 10. Backsheet 26 may be designed to prevent the exudates absorbed by and contained within the absorbent article 10 from soiling articles that may contact the absorbent article 10, such as bed sheets and undergarments. In certain embodiments, the backsheet 26 is substantially water-impermeable.

Suitable backsheet 26 materials include films such as those manufactured by Tredegar Industries Inc. of Terre Haute, Ind. and sold under the trade names X15306, X10962, and X10964. Other suitable backsheet 26 materials may include breathable materials that permit vapors to escape from the absorbent article 10 while still preventing exudates from passing through the backsheet 26. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

Backsheet 26 may also consist of more than one layer. The backsheet 26 may comprise an outer cover and an inner layer. A particularly suitable outer cover is available from Corovin GmbH, Peine, Germany as supplier code A18AH0. The outer cover may be made of a soft, non-woven material. The outer cover and an inner layer may be joined together by adhesive or any other suitable material or method.

The inner layer may be made of a substantially liquid-impermeable film 260, such as a polymeric film. An inner layer is a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385.

Suitable films may have a basis weight of from about 5 gsm to about 25 gsm; from about 15 gsm to about 25 gsm; from about 13 gsm to about 15 gsm; from about 12 gsm to about 14 gsm; from about 11 gsm to about 13 gsm; from about 8 gsm to about 12 gsm; less than about 25 gsm; less than about 20 gsm; less than about 15 gsm; greater than about 5 gsm; greater than about 8 gsm; greater than about 10 gsm. Basis weight measurements are made prior to activation.

Films may comprise from about 20 wt % to about 80 wt % of a polyolefin component. The polyolefin component may be selected from the group consisting of linear low density polyethylene polymers, low density polyethylene polymers, high density polyethylene polymers, polypropylene polymers, linear medium density polyethylene polymers, and mixtures thereof. Developments towards optimization of production processes of polyolefin resins may result in variants of the polyolefin versions mentioned in this group, which may also be suitable for this application. The polyolefin component may have a density of from about 0.91 $g/cm^3$ to about 0.95 $g/cm^3$.

The polyolefin component may be any of the class of thermoplastic polyolefin polymers or copolymers that are processable into a film or for direct lamination by melt extrusion onto the fibrous web. A number of thermoplastic polymers suitable in the practice of the invention are olefin based polymers including the most common ethylene or propylene based polymers such as polyethylene, polypropylene, and copolymers such as ethylene vinylacetate (EVA), ethylene methyl acrylate (EMA) and ethylene acrylic acid (EAA), or blends of such polyolefins.

Figure 4:
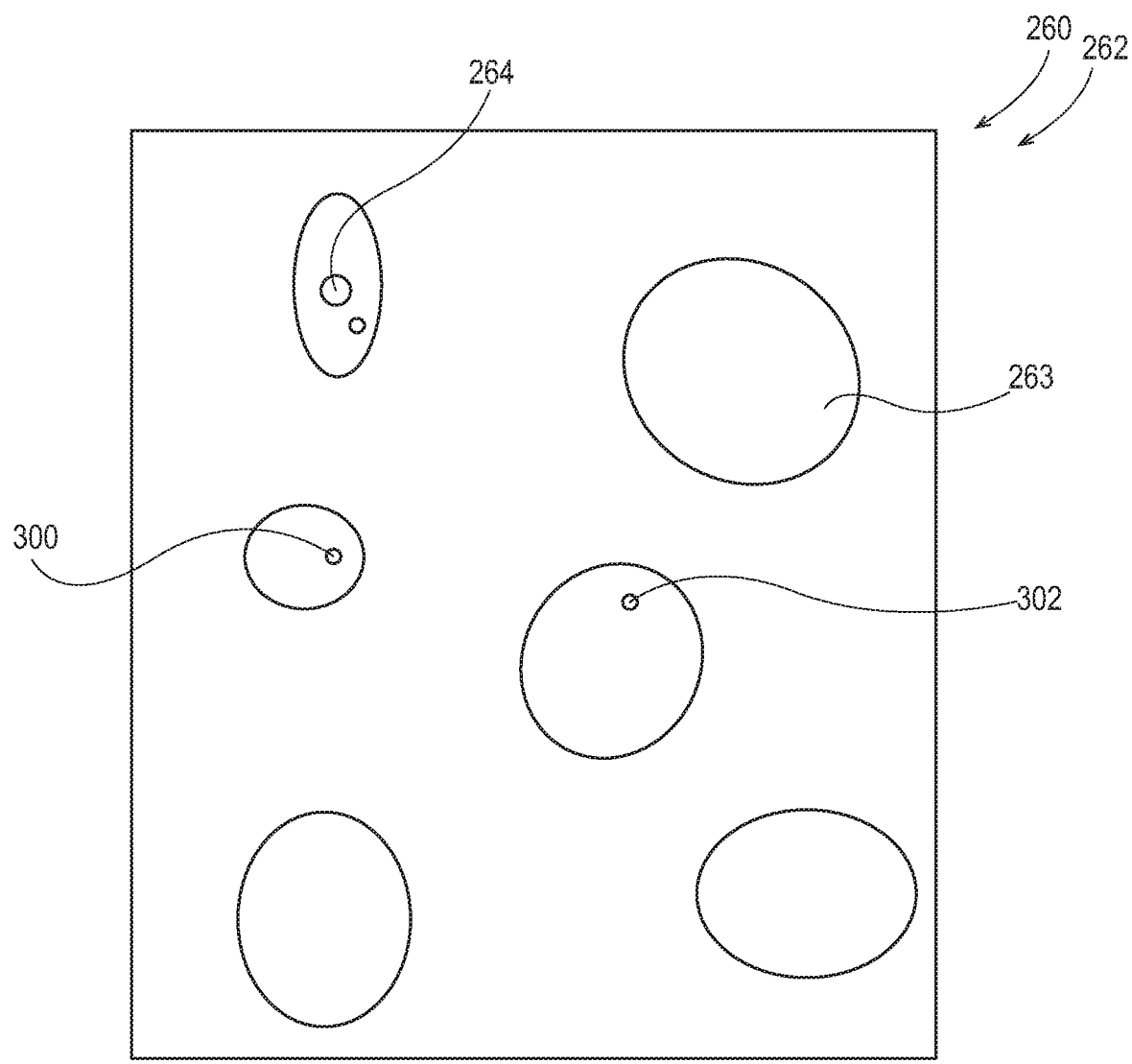
FIG. 4 is a schematic plan view of an exemplary embodiment of a backsheet.

Films suitable for the present invention may be breathable films 262 as shown in FIG. 4. Breathable films are polymeric films containing internal microporosities 263 (herein microporosities will be used interchangeably with "micropores"). Breathable films are described in U.S. Pat. No. 4,472,328.

The film 260 may be achieved by formulating a thermoplastic polymer with suitable additives and pore-forming fillers 264 to provide an extrudate or film. The film may be embossed using an embossing pattern or other method and stretched to create pores 263. $CaCO_3$ is commonly used as a pore-forming filler 264, other examples of pore forming fillers are sodium carbonate, talc, magnesium carbonate, barium sulfate, clays, kaolin and mica. The film in the invention also contains odor absorbing particle additives. Microporous-formable compositions of polyolefins, inorganic or organic pore-forming fillers 264 and other additives to make microporous sheet materials are known. This method may be done in line and provides economies in manufacturing and/or materials over known methods of making laminates. In addition, as developed above, microporous-formable polymer compositions may be obtained from blends of polymers such as a blend of an alkanoyl polymer and polyvinyl alcohol as described in U.S. Pat. No. 5,200,247. In addition, blends of an alkanoyl polymer, destructured starch and an ethylene copolymer may be used as the microporous-formable polymer composition as described in U.S. Pat. No. 5,407,979. With these polymer blends, it is unnecessary to use pore-forming fillers to provide microporosity upon incremental stretching. Rather, the different polymer phases in the film themselves, when the film is stretched at ambient or room temperature, produce microvoids.

Thermal stabilizers, UV stabilizers, antioxidants, antiblocking, lubricants, anti-static and slip agents and other additives may be added to the formula to improve the stability of the film when exposed to UV light, oxidizing agents, high temperatures and/or to aid in the production or processing of the resulting film. Examples of such additives include but are not limited to fatty amines, phenolic and phosphite antioxidant additives.

In some embodiments, the film 260 is monolayer. In other embodiments, the film comprises multiple layers, for example one or more skin layers and one or more core layers. Exemplary multilayer films are disclosed in US Pat. Pub. Nos. 2015/0104627 and 2012/0237746.

Additional Components

The absorbent article 10 may comprise one or more additional components known in the art, including but not limited to ears 60, fastening systems 62, waist features 64, leg cuffs 66, and hip panels 68 as illustrated in FIG. 1. One or more of said components may be joined to the chassis by an adhesive bond. Nonlimiting examples of potential adhesive bonds include leg cuff attachment bonds, cuff attachment bonds, ear attachment bonds, and fastener attachment bonds.

Further, said additional components and/or portions of the chassis 20 may comprise elastomeric materials with provide elasticity to said component/portion. Nonlimiting examples of elastomeric materials include films (e.g., polyurethane films, films derived from rubber and/or other polymeric materials), rubbers, SPANDEX®, elastic strands (e.g., LYCRA® strand, natural and/or synthetic rubber), an elastomeric coating applied to another substrate (e.g., a hot melt elastomer, an elastomeric adhesive, printed elastomer or elastomer co-extruded to another substrate), elastomeric nonwovens, scrims. Elastomeric materials can be formed from elastomeric polymers including polymers comprising styrene derivatives, polyesters, polyurethanes, polyether amides, polyolefins, combinations thereof or any suitable known elastomers including but not limited to co-extruded VISTAMAXX®. Exemplary elastomers and/or elastomeric materials are disclosed in U.S. Pat. Nos. 8,618,350; 6,410,129; 7,819,853; 8,795,809; 7,806,883; 6,677,258 and U.S. Pat. Pub. No. 2009/0258210. Commercially available elastomeric materials include KRATON (styrenic block copolymer; available from the Kraton Chemical Company, Houston, Tex.), SEPTON (styrenic block copolymer; available from Kuraray America, Inc., New York, N.Y.), VECTOR (styrenic block copolymer; available from TSRC Dexco Chemical Company, Houston, Tex.), ESTANE (polyurethane; available from Lubrizol, Inc., Ohio), PEBAX (polyether block amide; available from Arkema Chemicals, Philadelphia, Pa.), HYTREL (polyester; available from DuPont, Wilmington, Del.), VISTAMAXX (homopolyolefins and random copolymers, and blends of random copolymers, available from EXXON Mobile, Spring, Tex.) and VERSIFY (homopolyolefins and random copolymers, and blends of random copolymers, available from Dow Chemical Company, Midland, Mich.).

Figure 5:
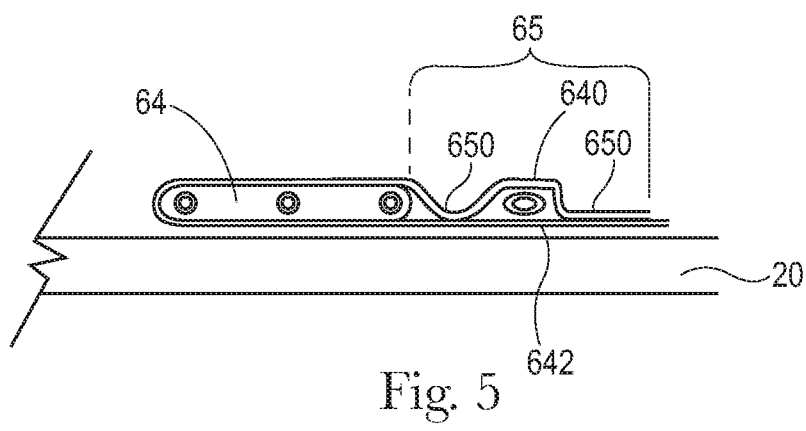
FIG. 5 is a schematic cross-sectional view of an exemplary waist feature.

In some embodiments, the article comprises one or more waist features 64. In some embodiments, one may be disposed in the first waist region 14 and the other may be disposed in the second waist region 18. In further embodiments, a waist feature 64 may comprise a closure bond region 65, as disclosed in U.S. Pat. App. No. 62/339,109. As shown in FIG. 5, the waist feature may comprise a top layer 640 and a bottom layer 642, and the top layer 640 is joined to the bottom layer 642 by one or more closure bonds 650. The closure bonds 650 may be formed by any suitable bonding technique or suitable combination of different bonding techniques. In one nonlimiting example, one or more closure bonds 650 comprise adhesive bonds.

The article may further comprises one or more hip panels 68 positioned in a waist region and/or in the crotch region as shown. Hip panels add stretch to the middle back of the article, permitting expansion of the back waist region and thereby creating a better fit about the hips and the buttocks of the wearer. An exemplary hip panel is disclosed in U.S. Pat. No. 5,575,783.

Odor Absorbing Material

Odors may stem from adhesives such as adhesives discussed above with respect to the core, adhesives that join various components to the chassis (leg cuff attachment bonds, waist feature attachment bonds); elastomeric materials such as those found in cuffs, hip panels, etc.; and/or inks and binding agents for example in wet indicators and printed designs. Inks may be printed on a number of article components including, but not limited to the backsheet, topsheet, cuffs, fastening tapes, wrappers, or any portion of the article. In some embodiments, the article comprises an aggregate adhesive content of at least about 1 gm, or from about 1 gm to about 5 gm, or from about 1.4 gm to about 3 gm, reciting for each range every 0.1 increment therein. In further embodiments, the article comprises an aggregate ink content of at least about 0.01 gm, or from about 0.01 gm to about 0.5 gm, or from about 0.012 gm to about 0.3 gm, or about 0.012 g to about 0.15 gm, reciting for each range every 0.05 increment therein. In still further embodiments, the article comprises an aggregate elastomeric content of at least about 0.2 g, from about 0.2 gm to about 1.2 gm, or from about 0.3 gram to about 1 gm, reciting for each range every 0.1 increment therein.

Returning to FIG. 4, an odor absorbing material 300 may be incorporated into the article, in particular into the backsheet 26. In this way, the backsheet can serve as trap or barrier to prevent odors from escaping the article 10. In some embodiments, the odor absorbing material 300 is provided within one or more micropores 263 of a breathable backsheet film 262. It is also contemplated that odor absorbing material may be incorporated into wrapper films and/or packaging.

The odor absorbing material may trap or inhibit odors via absorption or adsorption. Suitable odor absorbing materials include zeolites 302. Zeolites are crystalline aluminosilicates with an open three-dimensional framework structure that acts as a molecular sieve, separating molecules by size, shape or polarity. The open framework serves to trap volatile organic compounds. Moreover, by providing a zeolite in a micropore of a breathable film, the zeolite particle is more exposed to the volatile organic compounds and not buried within the film structure or within other components of the article. Essentially, the micropores create channels that allow odorous compounds to travel through the film and access the zeolites and/or other odor absorbing materials. Further, incorporating zeolite particles in the film micropores avoids dust and dust handling systems which may arise from the use of loose zeolite particles in an absorbent article. Incorporating zeolite particles into film micropores on a production line does not require additional equipment, which in turn saves energy, maintenance and equipment costs.

Zeolites differ by their frameworks, and the framework structures determine the effectiveness of a zeolite to trap certain molecules. Zeolites can be naturally occurring or synthetic. In some embodiments, zeolites can be hydrophobic, which may enhance its ability to absorb organic solvents. Nonlimiting examples of zeolites include Linde Type A, Linde Type X, Linde Type Y, Linde Type B, Linde Type F, Linde Type W, beta zeolites, ZSM-5 and SSZ-32. In some embodiments, the odor absorbing material is a Linde Type X (zeolite X), Linde Type Y (zeolite Y) and/or a combination thereof. In further embodiments, the odor absorbing material comprises a cation-containing zeolite. In one nonlimiting example, the zeolite comprises a sodium zeolite. In some nonlimiting examples, the sodium zeolite comprises about 30 wt % or less, or 20 wt % or less of sodium. Generally, a zeolite framework may be altered by the presence of a cation, such that the shape or size of the open framework is changed. Molecules that pass through cation-containing zeolites can be adsorbed or adhered to the surface of said zeolite by Van der Waals forces, covalent bonds or electrostatic attraction. In some embodiments, zeolites comprise a silica to aluminum ratio of about 1.5 or greater or about 1.6 or greater.

Odor absorbing materials 300, such as zeolites 302, may be provided in the form of masterbatches, which may be processed along with one or more polyolefin resins to form a film. Suitable zeolites are selected from a thermally stable family and able to maintain their efficacy after processing at high temperatures. Zeolites and/or films may be treated with a coating to avoid agglomeration of the zeolite particles and/or film defects. Exemplary zeolites are available from PQ Corporation of Malvern, Pa. under product code Adver XJ7BD and CBV 712. Additional exemplary odor absorbing materials include product codes 102995-N, 1000536-N and 1000258-E available from Ampacet of Tarrytown, N.Y.

In some embodiments, odor absorbing materials 300 comprise at least about 1 wt %, or at least about 3 wt %, or at least about 10 wt %, at least about 12 wt %, or from about 5 wt % to about 50 wt % of the film, reciting for each range every 10% increment therein. Where a film comprises more than one layer, zeolites may be provided in one layer, or in more than one layer, and/or in each layer.

In further embodiments, the article may comprise a ratio of aggregate odor absorbing content (i.e., mass of odor absorbing material) to aggregate adhesive content (i.e., mass of adhesives) ("Ratio of OAM to Adhesive" hereinafter) of at least about 0.5%, or at least about 1%, or from about 0.5% to about 10%, from about 0.9% to about 5%, reciting for each range every 0.1% increment therein. Alternatively or additionally, the article may comprise a ratio of aggregate odor absorbing material content to aggregate elastomeric content of at least about 5%, or from about 5% to about 20%, or from about 9% to about 15%, reciting for each range every 1% increment therein.

Additional components such as pigments or filler particles can be added to the film to provide a desired color effect, provide opacity, improve film properties or reduce the usage of resin. In one nonlimiting example, calcium carbonate is disposed in one or more film micropores. Further, additional processing steps can be done to improve tactile feel, drape or opacity.

Examples

The effectiveness of a selected odor absorbing material to eliminate the odors of non-perfumed diapers was confirmed using an expert odor panel. Panelists were screened for their ability to detect odors using an odor identification test capable of providing an absolute index of smell loss and an index for detecting malingering. An example of a suitable test is the UPSIT or Smell Identification Test available through Sensonics, Inc., P.O. Box 112, Haddon Heights, N.J. 08035 USA. Panelists were accepted for inclusion in the expert odor panel when they scored at least 75% on this test. Panelists who had any nasal impairment which rendered them deficient in their olfactory abilities were excluded. Panelists were not permitted to wear heavily scented products and were not permitted to eat, drink, chew gum or smoke 15 minutes prior to the odor evaluation.

Prior to odor evaluation, samples were placed into 2-liter wide mouth short profile glass jars with lids and aged. A suitable jar has a neck diameter of 143 mm and a neck height of 159 mm. An example of such a jar is item #320-2000 purchased from ThermoFischer Scientific. For each sample, one sample jar was created for each panelist. Diapers were opened up and stretched out with the front and back ears unfolded. Each diaper was placed on its side into a glass jar with the garment facing side of the diaper oriented toward the walls of the jar with no material protruding into the neck of the jar. For this test, unperfumed diapers were used as the control and as the foundation for testing odor absorbing materials. The unperfumed diapers each comprised an absorbent core that is substantially cellulose free.

Core Examples (Examples B-D below): 10 g of the material per square meter of topsheet was placed inside the core of the unperfumed diaper prior to placing it into a jar. A 1.5 inch slit was made through the backsheet of the diaper in the longitudinal direction, centered at the intersection of the longitudinal and latitudinal midpoints. A small pocket was carefully created in the core of the diaper and the zeolite material was placed inside. The backsheet was then repositioned over the exposed core prior to placement of the diaper into a jar.

Film Examples (Examples G-H and J-M): A piece of odor absorbing polyethylene film was cut to the same dimensions as the diaper's topsheet and then placed over the topsheet of the unperfumed diaper prior to placement into a jar.

The jars were tightly closed and aged at room temperature (21° C.±2° C.) for at least 16 hours in an odor free room with adequate air recirculation. For odor evaluation, each panelist opened the jar, smelled the sample and rated the odor. An intensity scale from 0 to 100 was used, with 100 indicating the most intense odor, 50 indicating a moderate odor and 0 indicating no detectable odor. The panelists also documented the character of the odor with descriptors of their choice that best described the odor.

Table 1 below shows a comparison of different odor absorbing materials disposed in an absorbent core. Examples A-D each comprise an unscented diaper manufactured by The Procter & Gamble Company in April 2016 in China, size 4, under production number EO XQ01516-006 ("Diaper A"). Diaper A comprises an absorbent core that is substantially cellulose free and a topsheet measuring 206 mm wide and 488 mm long.

As shown in Table 1, various odor absorbing materials were tested and found to be effective in reducing the malodor of dry products and changing the character of the malodor smell from a strong solvent smell to more acceptable paper, milky, earthy smells.

TABLE 1

Core Examples

| Example | Description of Odor Absorbing Material Added to the Absorbent Core | Malodor Intensity | Malodor Character |
| --- | --- | --- | --- |
| Comparative Example A | N/A—no odor absorbing material added | 30 | Solvent, plastic/rubber, dirty/oily |
| Inventive Example B | 1 g zeolite available from PQ Corp. under product name CBV 712 | 10 | Wet soil/moss, dirty/earthy |
| Inventive Example C | 1 g of zeolite available from PQ Corp. under product name Adver XJ7BD | 15 | Paper, cardboard, medicinal |
| Inventive Example D | 1 g of odor control raw material used to make masterbatch product code 102995-N available from Ampacet | 10 | green/chemical, slight plastic smell, medicinal |

The tables below show comparisons of examples which include films having different amounts of odor absorbing material. Examples E-M each comprise an unscented diaper, manufactured by The Procter & Gamble Company in China in November 2015, size 4, under production number EO BCT15-0325 ("Diaper B"). Diaper B comprises a substantially cellulose free absorbent core and a topsheet measuring 206 mm wide and 488 mm long.

Examples E-H and L-M were tested in May 2016 in accordance with the testing method above. Examples I-K were tested in August 2016 in accordance with the testing method above.

Table 2 below shows monolayer films used in the Examples. Comparative Examples E and I each comprise Diaper B. Comparative Example F comprises Diaper B and a film laid over its topsheet. The film is a polyethylene film containing 35 wt % calcium carbonate filler. The film was produced in April 2016.

Inventive Examples G-H and Inventive Examples J-K each comprise Diaper B and a film laid over the diaper's topsheet. The film in each of the Inventive Examples is a polyethylene film having some amount of odor absorbing material replacing calcium carbonate filler as detailed in Table 2 below. The odor absorbing material was provided in the form of a masterbatch produced with odor absorbing raw material (available from Ampacet under product code 102995-N or MB 1000536-E) and used in the extrusion of films. The masterbatch MB 1000536 was used for Inventive Example J. The remaining film Inventive Examples were produced using MB 102995-N. Both masterbatches include the same odor absorbing raw material at the same concentration. The films in Examples G-H and J-K differ in the amount of odor absorbing material and/or in the breathability values as determined by INDA IST 70.4 (01). Film basis weights were determined in accordance with methods ASTM D 756, ISO 536 & ERT-40.3-90 following the instructions for thin materials. Breathability of the film is tested using INDA IST 70.4 (01).

Inventive Examples J and K are more breathable films. Breathable films tend to comprise a greater wt % of $CaCO_3$, as a pore forming filler to increase the breathability. The polyethylene film used in Inventive Examples J and K is Hycare M-p-V1, available from RKW Group of Germany, modified by replacing 4 wt % of CaCO3 with 4 wt % of the odor absorbing material, such that the modified film comprises 4 wt % of odor absorbing material.

TABLE 2

Example Monolayer Film Descriptions

| Example | Film Basis Weight gsm | $CaCO_3$ and/or Odor Absorbing Material Content (wt % relative to film) | Ratio of OAM to Adhesive | Film Breathability $g/(m^2 \ast 24 \text{ hrs})$ |
| --- | --- | --- | --- | --- |
| Comparative Example E | n/a | No Film | n/a | n/a |
| Comparative Example F | 19.8 | 35 wt % $CaCO_3$; 0 wt % Odor Absorbing Material | 0 | 109 |
| Inventive Example G | 20.3 | 33.4 wt % $CaCO_3$; 1.6 wt % Odor Absorbing Material | 2.42% | 134 |
| Inventive Example H | 24.0 | 32 wt % $CaCO_3$; 3.0 wt % Odor Absorbing Material | 5.37% | 65 |
| Comparative Example I | n/a | No Film | n/a | n/a |
| Inventive Example J | 14.0 | 4.0 wt % Odor Absorbing Material | 1.67% | 13900 |
| Inventive Example K | 14.9 | 4.0 wt % Odor Absorbing Material | 1.78% | 12200 |

Table 3 shows a comparison of films. Examples E-H were tested in May 2016 in accordance with the testing method above. Examples F-H were each produced in April 2016 and were each activated using intermeshing rolls of 60 pitch and a depth of engagement of 0.25 inches. As shown in Table 3, films containing at least 3% of zeolite by weight were able to decrease odor intensity of the unscented diaper after 24 hrs.

TABLE 3

Reduction in Malodor

| Example | CaCO₃ and/or Odor Absorbing Material Content (wt % relative to film) | Ratio of OAM to Adhesive | Malodor Intensity | Malodor Character | % Reduction in Malodor Intensity (versus Example E) |
|---|---|---|---|---|---|
| Comparative Example E | No Film | n/a | 35 | Plastic, Solvent | n/a |
| Comparative Example F | 35 wt % CaCO₃; 0 wt % Odor Absorbing Material | 0 | 30 | Plastic, Antiseptic, Green | 14.3% |
| Inventive Example G | 33.4 wt % CaCO₃; 1.6 wt % Odor Absorbing Material | 2.42% | 30 | Plastic, Antiseptic, green | 14.3% |
| Inventive Example H | 32 wt % CaCO₃; 3.0 wt % Odor Absorbing Material | 5.37% | 25 | Antiseptic, green | 28.6% |

In addition, as can be seen in Table 4, more odor reduction per gram of odor absorbing material was achieved with increasing levels of breathability of the film. Films with odor absorbing materials at very low levels (Ratio of OAM to Adhesive of 1-2%) but with breathability levels above 10,000 g/(m²*24 hrs) will result in meaningful odor reductions while minimizing the use of odor absorbent materials and cost (compare Inventive Examples J and K with Inventive Example G). The polyethylene film used in Inventive Examples J and K is Hycare M-p-V1, available from RKW Group of Germany, modified by replacing 4 wt % of CaCO3 with 4 wt % of the odor absorbing material, such that the modified film comprises 4 wt % of odor absorbing material. The films were modified as stated in July 2016. The panelist odor testing was conducted in August 2016.

reduction is increased. Inventive Examples L and M each comprise Diaper B and a multilayered film laid over the diaper's topsheet. The layer of the film facing the topsheet comprises odor absorbing material. The odor absorbing material was provided in the form of a masterbatch produced with odor absorbing raw material (available from Ampacet under product code 102995-N) and used in the extrusion of films. Inventive Example L is a polyethylene film produced April 2016. Inventive Example M is a polyethylene film under trade name BP-137P from Clopay Corporation, Cincinnati, Ohio, modified by replacing 2 wt % of CaCO₃ with 2 wt % odor absorbing material in the topsheet facing layer, such that the modified film comprises 2 wt % odor absorbing material based on the total weight of the film, and 10 wt % odor absorbing material based on the weight of the topsheet facing layer. The modified film was produced in April 2016.

TABLE 4

Breathable Films

| Example | Odor Absorbing Material Content (wt % relative to film) | Ratio of OAM to Adhesive | Film Breathability g/(m²*24 hrs) | Malodor Intensity | Malodor Character | % Reduction in Malodor Intensity |
|---|---|---|---|---|---|---|
| Inventive Example G (not highly breathable) | 1.6 wt % Odor Absorbing Material | 2.42% | 134 | 30 | Plastic, Antiseptic, green | 14.3% (versus Example E) |
| Comparative Example I | 0% | n/a | n/a | 40 | solvent, plastic, green, chemical | n/a |
| Inventive Example J | 4.0 wt % Odor Absorbing Material | 1.67% | 13900 | 25 | solvent | 38% (versus Example I) |
| Inventive Example K | 4.0 wt % Odor Absorbing Material | 1.78% | 12200 | 20 | Plastic, solvent, white glue | 50% (versus Example I) |

Table 5 shows multilayer films. As shown in Tables 5-6, when a multilayer film comprises odor absorbing material in the layer facing the unscented diaper, the efficacy of odor Both films were activated using intermeshing rolls of 60 pitch and a depth of engagement of 0.25 inches. The panelist odor testing was conducted in May 2016.

TABLE 5

Comparison with Multilayer Films

| Example | Film Basis Weight gsm | | CaCO₃ and/or Odor Absorbing Material Content |
|---|---|---|---|
| Inventive Example H (monolayer) | 24.0 | Monolayer | 32 wt % CaCO₃; 3.0 wt % Odor Absorbing Material |
| Inventive Example L (multilayer, all odor absorbing material in topsheet-facing layer) | 20.2 | Topsheet facing layer | 25 wt % CaCO₃ (per weight of layer); 10 wt % odor absorbing material (per total weight of the layer facing the topsheet) |
| | | Opposing layer | 35 wt % CaCO₃ (per weight of layer) 0 wt % odor absorbing material |
| | | Total odor absorbing content by total weight of film | 3.3 wt % odor absorbing material (per total weight of film) |
| Inventive Example M (multilayer, all odor absorbing material in topsheet-facing layer) | 19.6 | Topsheet facing layer | standard CaCO₃ amount provided in Clopay BP-137P 0 wt % odor absorbing material |
| | | Opposing layer | 10 wt % odor absorbing material replacing 10 wt % CaCO₃ (per total weight of the layer facing the topsheet) |
| | | Total odor absorbing content by total weight of film | 2.0 wt % odor absorbing material (per weight of film) |

TABLE 6

Multilayer Malodor Reduction

| Example | Ratio of OAM to Adhesive | Film Breathability g/(m²*24 hrs) | Malodor Intensity | Malodor Character | % Reduction in Malodor Intensity (versus Example E) |
|---|---|---|---|---|---|
| Inventive Example H (monolayer) | 5.37% | 65 | 25 | Antiseptic, green | 28.6% |
| Inventive Example L (multilayer, all odor absorbing material in topsheet-facing layer) | 4.97% | 50 | 20 | Antiseptic, Chemical | 43% |
| Inventive Example M (multilayer, all odor absorbing material in topsheet-facing layer) | 2.34% | 5546 | 22.5 | Antiseptic Green | 35.7% |

Combinations

A. An absorbent article a chassis comprising a topsheet, a backsheet, and an absorbent core disposed between the topsheet and backsheet; and a film comprising an odor absorbing material.

B. The absorbent article according paragraph A wherein backsheet comprises the film.

C. The absorbent article according to any of the preceding paragraphs wherein the absorbent core comprises absorbent particulate polymer material and about 10% or less by weight of cellulosic fibers.

D. The absorbent article according to paragraph C wherein the absorbent core comprises one or more adhesive materials to at least partially immobilize the absorbent particulate polymer material.

E. The absorbent article according to any of the preceding paragraphs wherein the film comprises a plurality of micropores, and wherein the odor absorbing material is disposed in one or more of the micropores.

F. The absorbent article according to any of the preceding paragraphs wherein the odor absorbing material comprises zeolites.

G. The absorbent article according to paragraph F wherein the zeolites comprise Zeolite X, ZSM-5 Zeolite Y and combinations thereof.

H. The absorbent article according to paragraphs F or G wherein the zeolites comprise a cation-containing zeolite.

I. The absorbent article according to paragraph F-H wherein the film comprises at least about 3.0% zeolites by weight.

J. The absorbent article according to paragraphs F-I wherein the film comprises more than one layer, and at least one layer comprises about at least about 10% zeolites by weight.

K. The absorbent article according to any of the preceding paragraphs further comprising:
   one or more adhesives forming an aggregate adhesive content; and
   an odor absorbing material disposed in the backsheet, wherein the odor absorbing material forms an aggregate odor absorber content;

wherein the ratio of the aggregate odor absorbent content to the aggregate adhesive content is about 0.5% to about 10%.

L. The absorbent article according to any of the preceding paragraphs further comprising:
a first waist feature joined to the chassis and disposed in the first waist region; and
a second waist feature joined to the chassis disposed in the second waist region.

M. The absorbent article according to paragraph L wherein the first and/or the second waist feature is elasticized.

N. The absorbent article according to paragraphs L or M wherein the first and/or the second waist feature comprise a closure bond region.

O. The absorbent article according to any of the preceding paragraphs further comprising an aggregate elastomeric content, and odor absorbing material forms an aggregate odor absorber content; and wherein the aggregate odor absorbing content to aggregate elastomeric content is from about 5% to about 20%.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
a chassis comprising a topsheet, a backsheet, an absorbent core disposed between the topsheet and the backsheet, and one or more adhesive materials forming an aggregate adhesive content;
wherein the absorbent core comprises an absorbent particulate polymer material and about 10% or less, by weight of the absorbent core, of cellulosic fibers;
wherein the backsheet comprises a monolayer film comprising a plurality of micropores, wherein the film comprises zeolites disposed in one or more of the micropores, wherein the zeolites disposed in the one or more of the micropores is at least partially incorporated into the film, and wherein the zeolites form an aggregate odor absorbing content; and
wherein a ratio of the aggregate odor absorbing content to the aggregate adhesive content is from about 0.5% to about 10%.

2. The absorbent article of claim 1 wherein the absorbent core comprises at least a portion of the one or more adhesive materials, and wherein the a portion of the one or more adhesive materials at least partially immobilizing the absorbent particulate polymer material.

3. The absorbent article of claim 1 wherein the zeolites comprise Zeolite X, ZSM-5, Zeolite Y, and combinations thereof.

4. The absorbent article of claim 1 wherein the film comprises at least 3.0% zeolites by weight.

5. The absorbent article of claim 1 wherein the zeolites comprise a cation-containing zeolite.

6. An absorbent article comprising:
a chassis comprising a topsheet, a backsheet comprising a film comprising a plurality of micropores, and an absorbent core disposed between the topsheet and the backsheet;
one or more adhesives forming an aggregate adhesive content; and
an odor absorbing material disposed in at least one of the micropores of the backsheet, wherein the odor absorbing material is at least partially integral with the backsheet, and wherein the odor absorbing material forms an aggregate odor absorbing content;
wherein a ratio of the aggregate odor absorbing content to the aggregate adhesive content is from about 0.5% to about 10%.

7. The absorbent article of claim 6 wherein the absorbent core comprises less than 5 wt % of cellulosic fibers.

8. The absorbent article of claim 6 wherein the film is a monolayer.

9. The absorbent article of claim 6 wherein the odor absorbing material comprises zeolites.

10. The absorbent article of claim 9 wherein the zeolites comprise Zeolite X, ZSM-5, Zeolite Y and combinations thereof.

11. The absorbent article of claim 9 wherein the zeolites comprise a cation-containing zeolite.

12. The absorbent article of claim 9 wherein the film comprises at least about 3.0% zeolites by weight.

13. The absorbent article of claim 9 wherein the film comprises two or more layers, and wherein at least one of the layers comprise at least 10% zeolites by weight.

14. The absorbent article of claim 13 wherein one of the two or more layers faces the absorbent core.

15. The absorbent article of claim 6 wherein the absorbent core is free of cellulosic fibers.

16. An absorbent article for wearing about the lower torso of a wearer, the absorbent article comprising:
a first waist region, a second waist region, a crotch region disposed between the first and second waist regions;
a chassis comprising a topsheet, a backsheet comprising a plurality of micropores, and an absorbent core disposed between the topsheet and the backsheet;
a first elasticized waist feature joined to the chassis and disposed in the first waist region;
a second elasticized waist feature joined to the chassis disposed in the second waist region; and
one or more adhesive materials forming an aggregate adhesive content;
wherein the backsheet comprises an odor absorbing material comprising zeolites, wherein the odor absorbing material is disposed in at least one of the plurality of micropores of the backsheet, wherein the odor absorbing material is at least partially integrated into the backsheet, and wherein the odor absorbing material forms an aggregate odor absorbing content; and wherein a ratio of the aggregate odor absorbing content to the aggregate adhesive content is from about 0.5% to about 10%.

17. The absorbent article of claim 16 wherein the odor absorbing material comprises zeolite X, ZSM-5, zeolite Y, and combinations thereof.

18. The absorbent article of claim 16 wherein the absorbent article comprises an elastic content, wherein the odor absorbing material forms an aggregate odor absorbing content, and wherein a ratio of elastic content to aggregate odor absorbing content is from about 5% to about 20%.

19. The absorbent article of claim 16 wherein the backsheet comprises a film, and wherein the film comprises at least 3.0% zeolites by weight.

* * * * *